United States Patent
Ziaie et al.

(10) Patent No.: US 10,772,560 B2
(45) Date of Patent: Sep. 15, 2020

(54) SKIN-MOUNTED HYDRATION SENSOR AND MANAGEMENT SYSTEM

(71) Applicant: Purdue Research Foundation, West Lafayette, IN (US)

(72) Inventors: Babak Ziaie, West Lafayette, IN (US); Manuel P. Ochoa, Lafayette, IN (US); Vaibhav Jain, West Lafayette, IN (US); Rahim Rahimi, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 233 days.

(21) Appl. No.: 15/723,157

(22) Filed: Oct. 2, 2017

(65) Prior Publication Data

US 2018/0249952 A1 Sep. 6, 2018

Related U.S. Application Data

(60) Provisional application No. 62/403,188, filed on Oct. 2, 2016.

(51) Int. Cl.
*A61B 5/00* (2006.01)
*A61B 5/145* (2006.01)
*A61B 5/053* (2006.01)

(52) U.S. Cl.
CPC ........ *A61B 5/4875* (2013.01); *A61B 5/14517* (2013.01); *A61B 5/6833* (2013.01); *A61B 5/0537* (2013.01); *A61B 2503/10* (2013.01); *A61B 2560/0412* (2013.01); *A61B 2562/0214* (2013.01); *A61B 2562/04* (2013.01); *A61B 2562/12* (2013.01)

(58) Field of Classification Search
CPC .. A61B 5/00; A61B 5/05; A61B 5/053; A61B 5/0531; A61B 5/0533; A61B 5/0537; A61B 5/4875; A61B 5/14507; A61B 5/14517; A61B 10/0045; A61B 2562/0214
See application file for complete search history.

(56) References Cited

U.S. PATENT DOCUMENTS

| | | | | |
|---|---|---|---|---|
| 5,638,815 A | * | 6/1997 | Schoendorfer | .... A61B 5/14521 600/346 |
| 2009/0308742 A1 | * | 12/2009 | Paranjape | ............ A61B 5/0537 204/403.1 |

(Continued)

*Primary Examiner* — Daniel L Cerioni
*Assistant Examiner* — Raymond P Dulman
(74) *Attorney, Agent, or Firm* — Purdue Research Foundation

(57) ABSTRACT

A wearable paper-based platform with simultaneous passive and active feedback for monitoring perspiration is provided. The sensor platform comprises two modules: a disposable wicking-based sweat collection patch with discrete colorimetric feedback, and a reusable electronic detachable module for active feedback. The disposable patch comprises a hygroscopic wicking material laminated between two polymeric films. The wicking material is patterned with a radial finger design that offers discretized visual readout of the sensor. The active module attaches to the film and alerts the user when the film collects a pre-determined volume of sweat. The multi-feedback system allows high-performance athletes who value objective quantification of perspiration to better assess their sweat loss during physical activities.

14 Claims, 9 Drawing Sheets

(56) References Cited

U.S. PATENT DOCUMENTS

| | | | |
|---|---|---|---|
| 2012/0150072 A1* | 6/2012 | Revol-Cavalier | ............................ A61B 5/14517 600/573 |
| 2014/0303462 A1* | 10/2014 | Ellenberger-Girard | ....................... A61B 5/6833 600/314 |
| 2015/0057515 A1* | 2/2015 | Hagen | ................. A61B 5/14546 600/346 |
| 2017/0119289 A1* | 5/2017 | Yoshioka | ........... A61B 5/14517 |
| 2017/0238854 A1* | 8/2017 | Henshaw | ............ A61B 5/14517 |
| 2017/0296114 A1* | 10/2017 | Ghaffari | ................ A61B 5/4266 |
| 2018/0020966 A1* | 1/2018 | Begtrup | ................... A61B 5/01 600/301 |
| 2018/0344259 A1* | 12/2018 | Pavlov | ................. A61B 5/0002 |
| 2019/0154603 A1* | 5/2019 | Suster | ................... G01N 27/026 |

\* cited by examiner

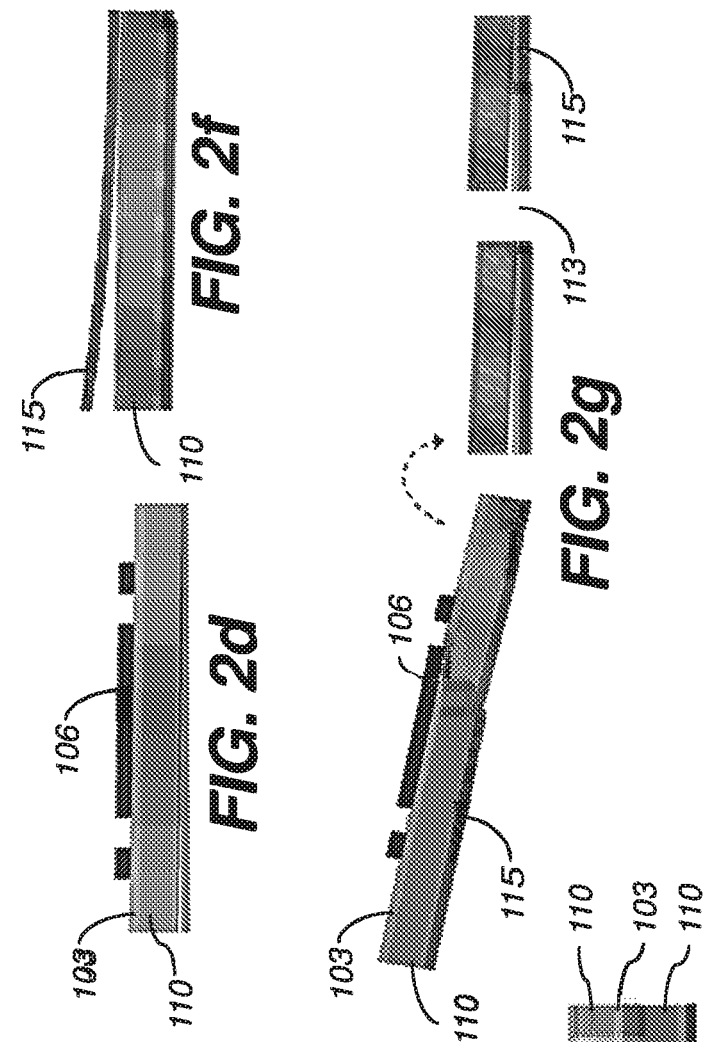

SKIN-MOUNTED HYDRATION SENSOR AND MANAGEMENT SYSTEM

CROSS-REFERENCE TO RELATED APPLICATIONS

The present application is related to and claims the priority benefit of U.S. Provisional Patent Application Ser. No. 62/403,188, filed Oct. 2, 2016, the contents of which are hereby incorporated by reference in their entirety into this disclosure.

STATEMENT OF GOVERNMENT SUPPORT

This invention was made with government support under EFRI 1240443 awarded by the National Science Foundation. The government has certain rights in the invention.

TECHNICAL FIELD

The present application relates to biosensing systems, and more specifically, to an integrated system for sensing and indicating a hydration level of a user based on sweat emitted from skin.

BACKGROUND

The state of hydration in humans is a delicate physiological parameter with direct effects on the functional performance at the cellular, organ, and systemic level. Studies have shown that deviations as small as 2% lower than normal levels of hydration (i.e., dehydration) can reduce cognitive and physical performance of a person by more than 30%. Unfortunately, monitoring hydration is neither straightforward nor standard practice; methods include analyzing markers of hydration such as serum ion concentration (invasive), urine color/osmolality, and body mass. Among these, acute changes in body mass and urine color are the most convenient techniques due to their non-invasive nature. However, each of these methods poses shortcomings, including the need for a (non-portable) scale for the mass technique, or the delayed indication of hydration (compared to plasma osmolality) in the urine method. Therefore, improvements are needed in the field.

SUMMARY

According to one aspect, the present disclosure provides a hydration indicator, comprising a hygroscopic arrangement including a common central region and a plurality of fingers of varying lengths, each finger starting at the common central region and terminating with an indicator, a first spacer centrally contacting a first side of the hygroscopic arrangement and configured to couple the hygroscopic arrangement to skin of a subject, and an adhesive layer centrally adhered to a second side opposite to the first side of the hygroscopic arrangement and configured to affix the hygroscopic arrangement to the skin of the subject and protect the hygroscopic arrangement from outside environment, the first spacer configured to include an opening centrally positioned about the common central region such that hydration from sweating is allowed to wick to the common central region through the opening and traverse down each of the plurality of fingers.

According to another aspect, a wearable paper-based platform with simultaneous passive and active feedback for monitoring perspiration is provided. The sensor platform comprises two modules: a disposable wicking-based sweat collection patch with discrete colorimetric feedback, and a reusable electronic detachable module for active feedback. The disposable patch comprises a hygroscopic wicking material laminated between two polymeric films. The wicking material is patterned with a radial finger design that offers discretized visual readout of the sensor. The film size is rapidly customizable using commercial laser engravers to accommodate a broad range of sweat rates and volumes. The active module attaches to the film and alerts the user when the film collects a pre-determined volume of sweat. The multi-feedback system allows high-performance athletes who value objective quantification of perspiration to better assess their sweat loss during physical activities.

BRIEF DESCRIPTION OF THE DRAWINGS

In the following description and drawings, identical reference numerals have been used, where possible, to designate identical features that are common to the drawings.

FIG. 2a is a first step of a fabrication process of the device of FIG. 1.

FIG. 2b is a second step of a fabrication process of the device of FIG. 1.

FIG. 2c is a third step of a fabrication process of the device of FIG. 1.

FIG. 2d is a fourth step of a fabrication process of the device of FIG. 1.

FIG. 2e is a fifth step of a fabrication process of the device of FIG. 1.

FIG. 2f is a sixth step of a fabrication process of the device of FIG. 1.

FIG. 2g is a seventh step of a fabrication process of the device of FIG. 1.

FIG. 2h is a eighth step of a fabrication process of the device of FIG. 1.

The attached drawings are for purposes of illustration and are not necessarily to scale

DETAILED DESCRIPTION

In the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Efficient and accurate measurement of perspiration requires occlusion of a specific dermal region and collection of all the sweat secreted from that area for the duration of the measurement. A hydrophobic dermal patch with an adhesive perimeter and an embedded hollow channel (for wicking out sweat) can provide one such structure for sweat collection; however, sweat droplets forming at the skin surface may require hours to generate sufficient sweat for wicking into the channel for reliable read-out. Instead if the channel is filled with a hygroscopic material, any sweat secreted onto the skin can be immediately wicked and collected in the hygroscopic material for read-out or transport. The present disclosure provides a device 100 that uses cellulose fiber in one non-limiting example as the wicking material. Rather than using a single channel, however, the device 100 comprises a radial array of channels of varying lengths that allow for quantization of the collected sweat for more objective and quantitative visual indication.

Figure 1A:
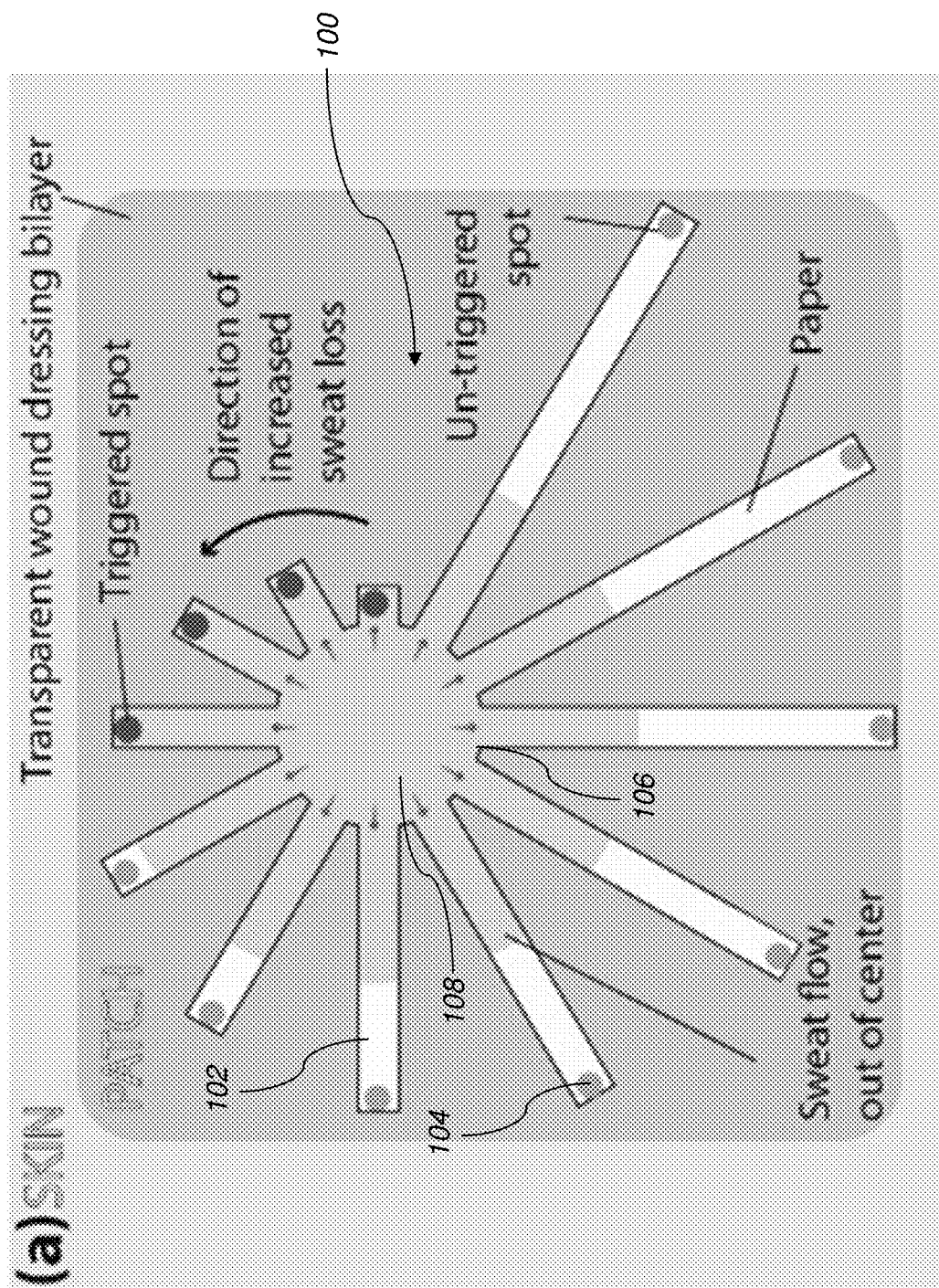
FIG. 1a is a diagram showing a top view of a skin-mounted hydration indicator device according to one embodiment.

A radial design of a hydration indicator device 100 according to one embodiment is illustrated in FIG. 1a. The device 100 includes a substrate 106 having a central region 108 and discretized channels or fingers 102 extending radially outward from the central region 108 in increasing order of length as shown to allow chronological tracking of fluid due to a substantially uniform flow rate in each finger 102 achieved by the circular pattern. The device 100 also provides easy loading of dyes, which are applied at the distal ends 104 of the fingers to provide visual cues to the user and/or detect specific analytes in sweat. The dye indicators at the channel distal ends therefore change color chronologically, with the end of the shortest channel changing color first, and the end of the longest channel changing color last. As the channel ends change color in succession, the user may be reminded that it is time to replace the fluid lost to sweat (take a drink). The substrate is sandwiched between two films 110 of a waterproof material having a port 113 on one side from which the fluid (sweat) can enter the substrate 106. To maintain the uniformity of flow in the fingers 102, the port is preferably concentric and its diameter is preferably less than or equal to the central circular region 108 of the substrate 106.

The number of fingers 102 and spacing between them depend on the resolution of feedback desired which in turn depends on the total time of application and user preferences, which in turn will give the total number of fingers (N) in the device 100. The methodology for computing the parameter values according to the application depends on various parameters which are defined below. In two examples, to determine the practicality of this design, the patch parameters required for measuring sweat rate were computed assuming two cases: a person at rest using the patch for 30 minutes and a person exercising for 8 hours (such as in a marathon). The computed parameter values are shown in Table 1 below; the resulting patches would have dimensions which are reasonable for being worn unobtrusively.

TABLE 1

Table for values in two example cases

| Design Parameter | Resting individual | Exercising individual |
|---|---|---|
| Time of application, T (min) | 30 | 480 |
| Sweating Rate, $SR\left(\frac{mg}{cm^2 * min}\right)$ | 0.25 | 0.9 |
| Paper Thickness, t (μm) | 50 | 500 |
| r (mm) | 5 | 10 |
| Radius of port, $r_1$ (mm) | 4.08 | 3.4 |
| Resolution desired, R (min) | 10 | 30 |
| Number of fingers, n | 3 | 16 |
| Gap b/w fingers, $m_i$ (mm) | 2 | 2 |
| Width of the fingers, w (mm) | 2.1 | 1.02 |

Numerous hygroscopic materials and hydrophobic films can be used as the substrate 106 and encapsulating layers 110, respectively, of the device 100. In one embodiment, a medical polymeric wound dressing, such as Opsite transparent film, may be used as the encapsulating layer 110 due to its commercial availability and established use in clinics. Suitable materials for the substrate wicking material 106 include, but are not limited to: cellulose acetate, filter paper, and nitrocellulose. The experiments below show that of these three, filter paper provides a reliable, mechanically robust, and economical solution for substrate 106.

Figure 1B:
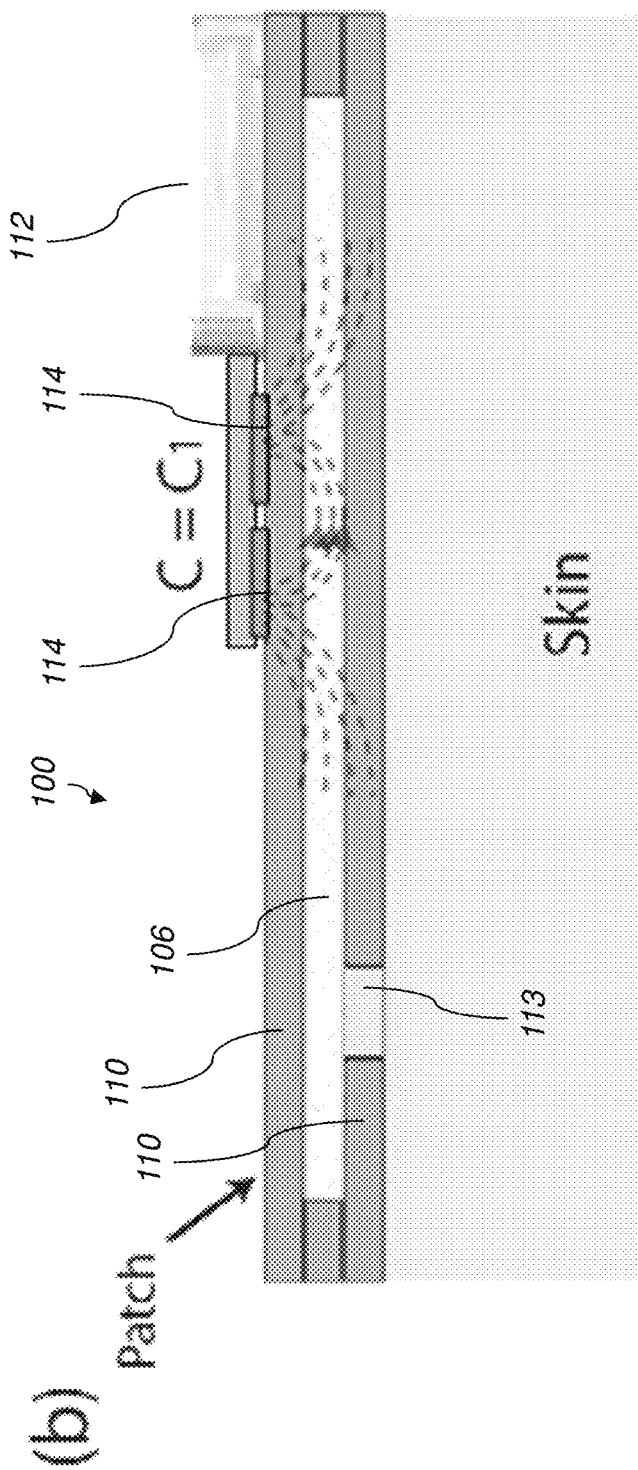
FIG. 1b is a diagram showing a side view of the hydration indicator device of FIG. 1 when initially applied to a user's skin.
Figure 1C:
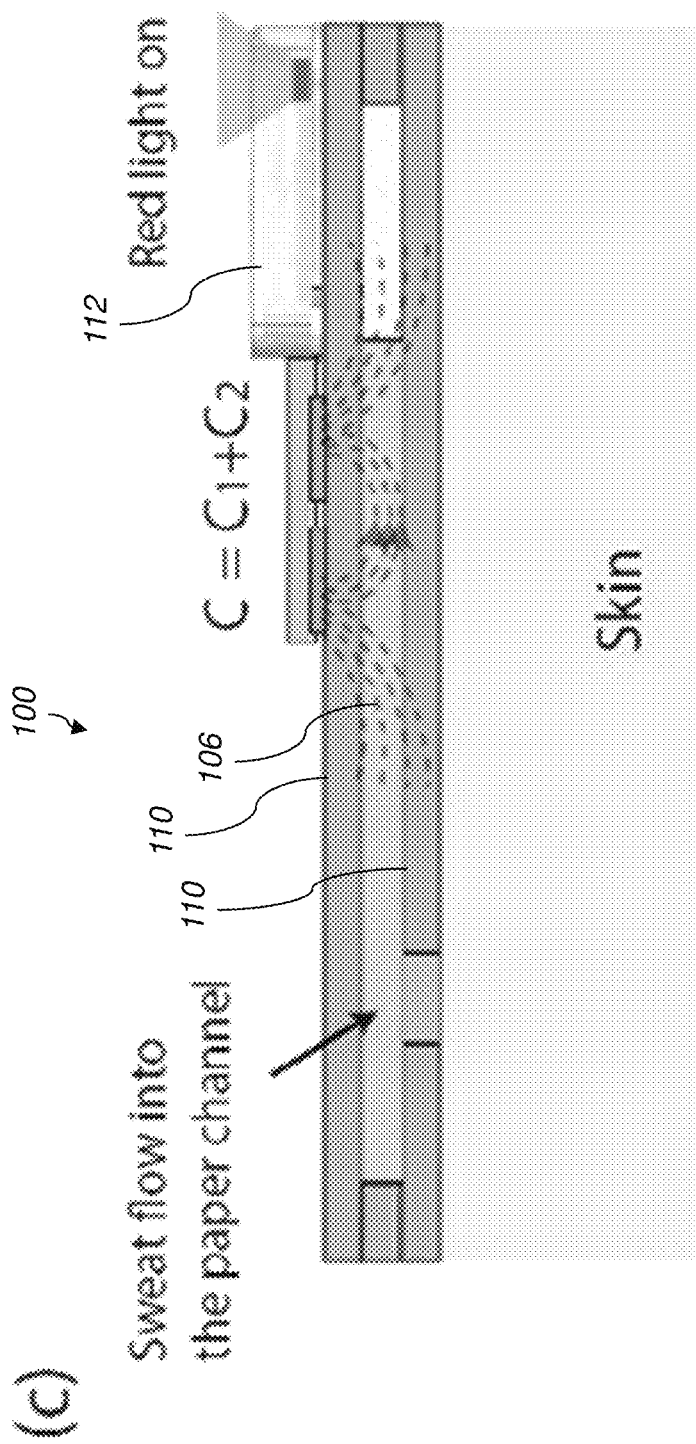
FIG. 1c is a diagram showing a side view of the hydration indicator device of FIG. 1 after the user's sweat has been absorbed into a channel of the indicator device.

In one embodiment, an active control module 112 is provided which attaches to the film and alerts the user when the substrate 106 collects a pre-determined volume of sweat. The working principle of the active module 112 is illustrated in FIGS. 1b and 1c. The active module 112 is worn overlapping one finger 102 of the patch. As the finger 102 becomes saturated with sweat, the circuit senses a change in capacitance providing an electrical feedback (In this case, an LED, but a haptic or an audio alert may be used instead). The capacitive sensing material comprises two side-by-side electrodes 114 (e.g., comprising copper or other electrically conductive material) that are placed on either side of a piece of parchment paper to prevent short circuiting. The electrodes 114 are preferably placed side-by-side rather than stacked to maximize the capacitor fringe effect, thus increasing the sensor's sensitivity to outside disturbance. The capacitor is placed in parallel with a resistor, and by measuring the time to discharge, we quantify the sensor's capacitance. In one embodiment, the active module 112 includes a microcontroller (not shown), such as a MSP430G2553 microcontroller, which is connected to the electrodes and programmed to charge the RC circuit until it reaches a stable, DC voltage. Then, the output charging pin changes to an input capturing pin and a stable clock begins to track time. When the voltage across the undriven, decaying RC circuit crosses the logic level low threshold, the time is recorded. This time is expected to be higher with increasing capacitance values. The microcontroller can easily be programmed to respond to the capacitance value. For example, if it senses a capacitance value above a threshold, it can notify the user by asserting an LED or haptic feedback device connected to the microcontroller. The notification device (LED, haptic device, or the like) may be connected to the microcontroller in a wired or wireless manner. The MSP430G2553 was chosen in the illustrated example due to its "ultra-low power" consumption as well as the breadth of developer resources available. However, it shall be understood that other types of microprocessors and associated memory may also be used.

In one embodiment, the device 100 may be fabricated according to a process as shown in FIG. 2. As shown in FIG. 2a, the wicking material 106 is first cut (laser-machined) into the multi-channel pattern (FIG. 2b). Next, a dye which changes color when wetted by sweat (e.g., KMnO4 or $CoCl_2$ (or $CoCl_2*2H_2O$), which changes from blue to magenta when wetted) is deposited at ends 104 of the channels 102. In one example, the dye is deposited via a stamping technique. Then we expose adhesive 103 of one Opsite film 110 and attach the wicking material 106 (FIGS. 2C and 2d). One piece of the dressing film 110 is then cut (e.g. laser-machined) to create a port 113 (FIG. 2g). The three layers are then stacked (FIG. 2h) such that the hole 113 in the bottom layer film 110 is concentric with the circle in the wicking material pattern. During use, the backings 115 are removed, and the wicking material 106 is exposed to the skin via the hole.

In one example, a prototype of the active module 112 was fabricated on a custom circuit board. The active module comprises a capacitive sensor circuit on a custom PCB designed to detect change in the material properties of the patch at the end of the tip when water comes to the finger end. A single-sided PCB was laser-machined from adhesive copper tape laminated onto a glass slide. The PCB traces were defined on the copper using a commercial YAG laser engraver system (PLS6MW, ULS Inc.), with parameters of a 40 W 1.06 µm fiber laser set to 20% speed and 80% power at 30 kHz frequency. The negative areas were peeled away and then the components were soldered together. This process can be adapted to large-scale sheet-to-sheet or roll-to-roll production. For production, the circuit may be fabricated on a standard flexible printed circuit board.

Figure 3:
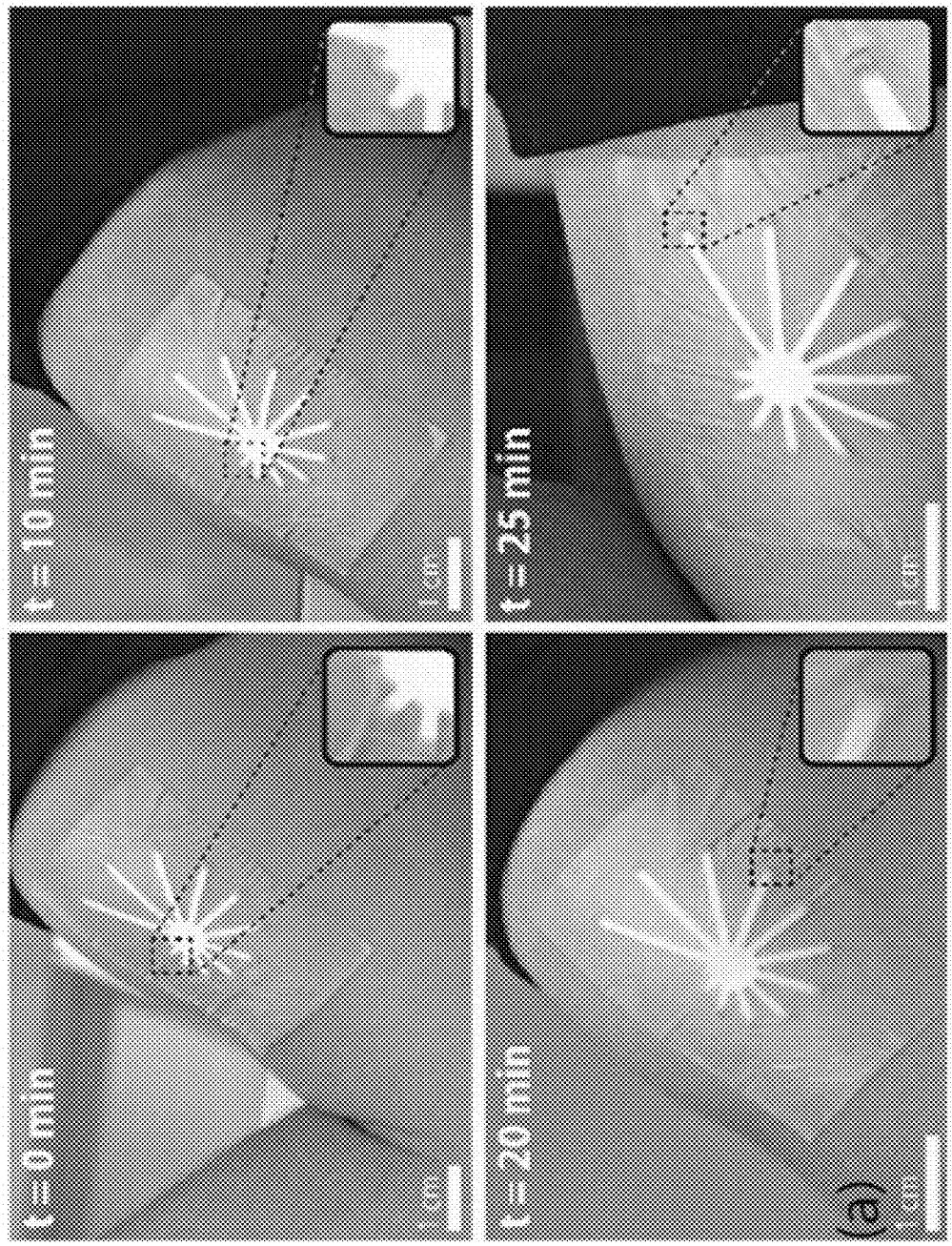
FIG. 3 is a photograph showing four chronological stages of hydration indication of the device of FIG. 1 when worn by a user.

The completed device 100 is shown in FIG. 3 on a user's arm. A prototype of the device 100 is shown in FIG. 4a in practical use (i.e., worn by an athlete during an aerobic workout). The device 100 can flex sufficiently to conform to the athlete's skin, and it remains attached to the skin throughout the workout. Furthermore, the device 100 readout is visible in standard gymnasium lighting. These qualitative investigations demonstrate that the patch is a practical wearable device with sufficient robustness for active wear. FIGS. 4b and 4c show the prototype feedback device and 4d and 4e show the device working in conjunction with the patch.

The fabrication process comprises only 3 major steps and relies on paper as the substrate in one embodiment (but may comprise other commercial fibrous meshes), thereby enabling a variety of low-cost and scalable manufacturing options. For example, the device 100 can also be made through inkjet printing/screen printing the dye on a die/laser cut paper or wax printed design on paper followed by packing of the Opsite film through lamination in a roll-to-roll manner to increase the throughput for mass production.

Figure 4:
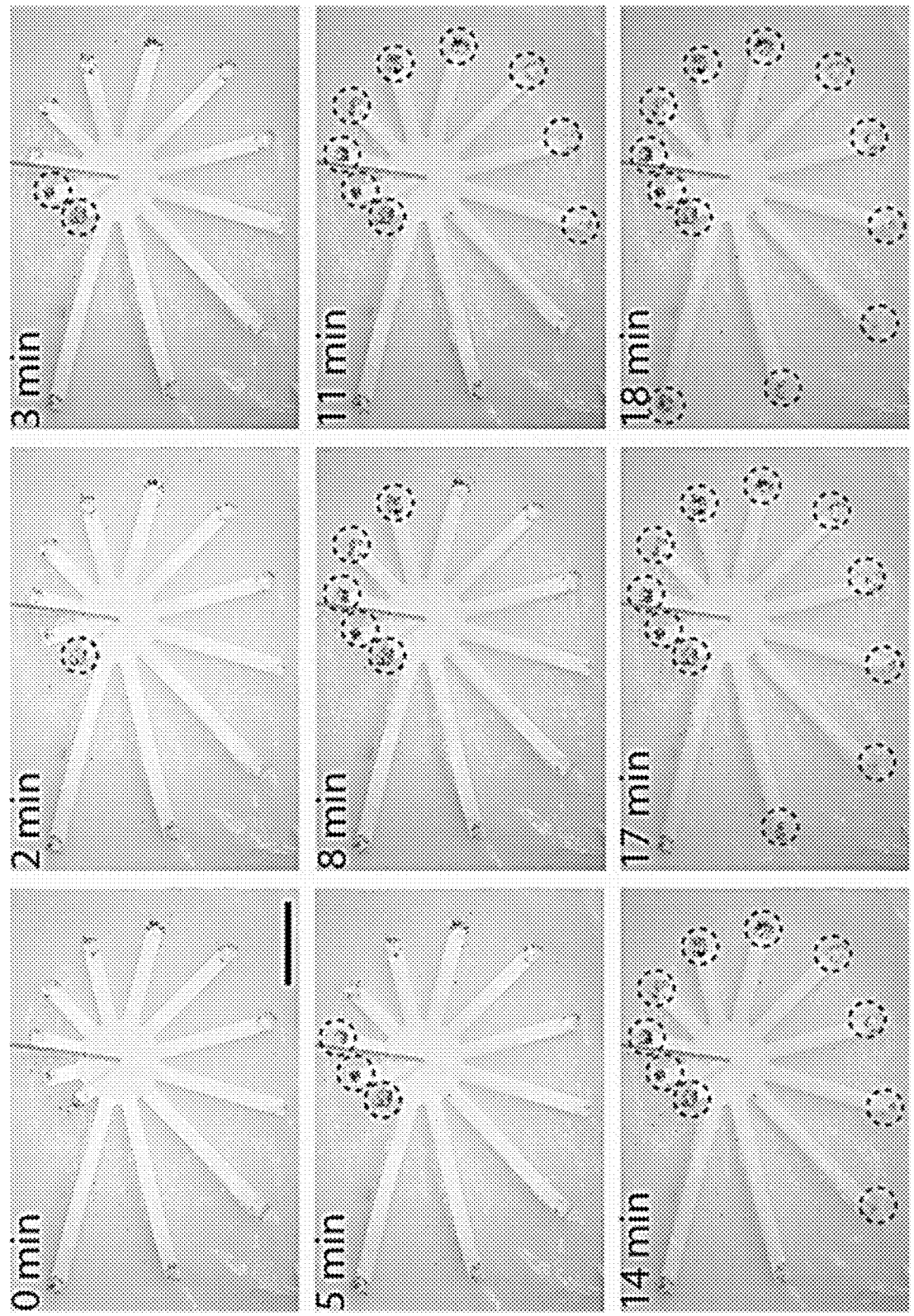
FIG. 4 is a photograph of successive stages of hydration indication of the device of FIG. 1.
Figure 5:
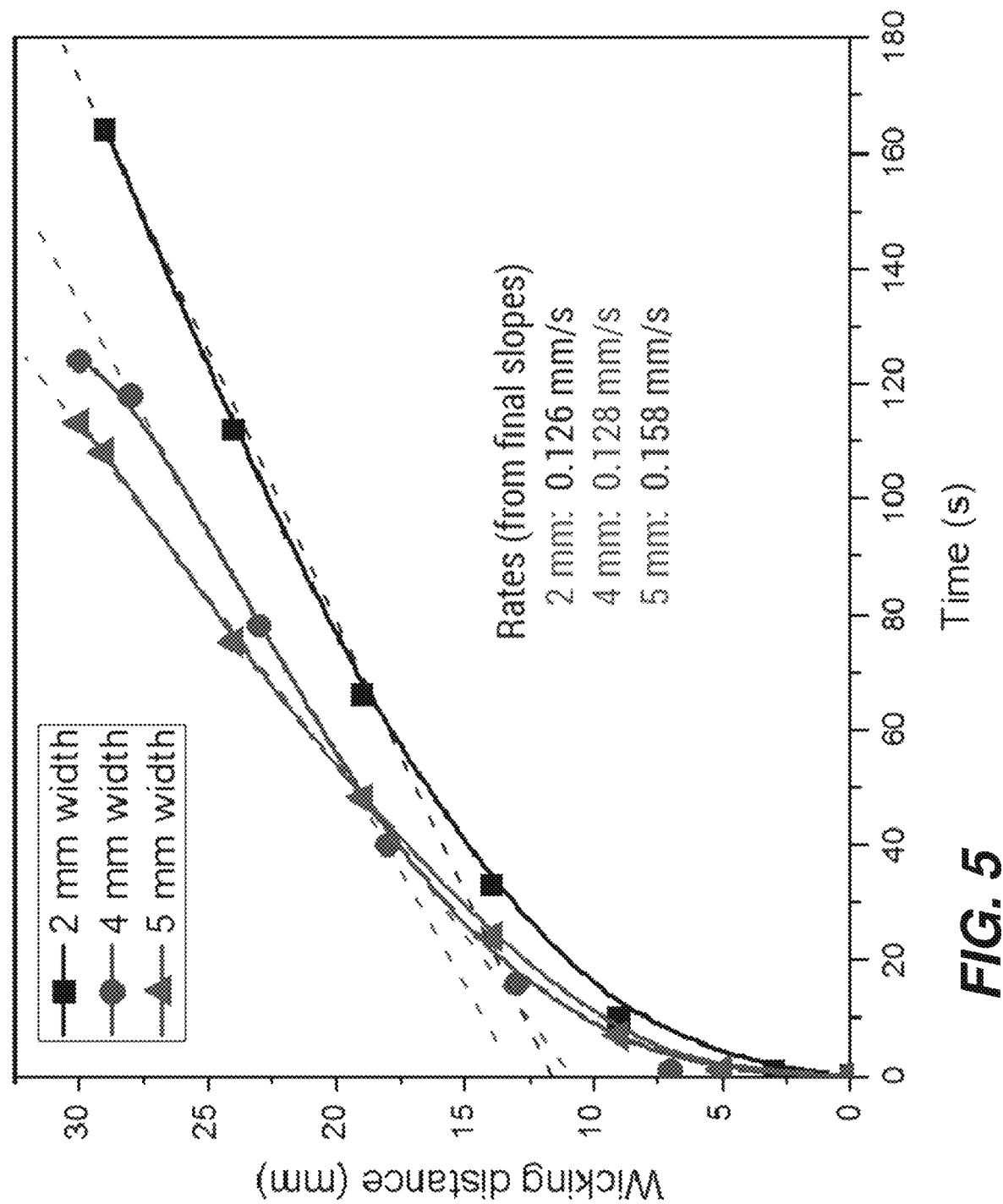
FIG. 5 is a graph showing wicking rate of water on strips of filter paper/Opposite bilayer for various strip widths (length=3 cm for all samples).
Figure 6:
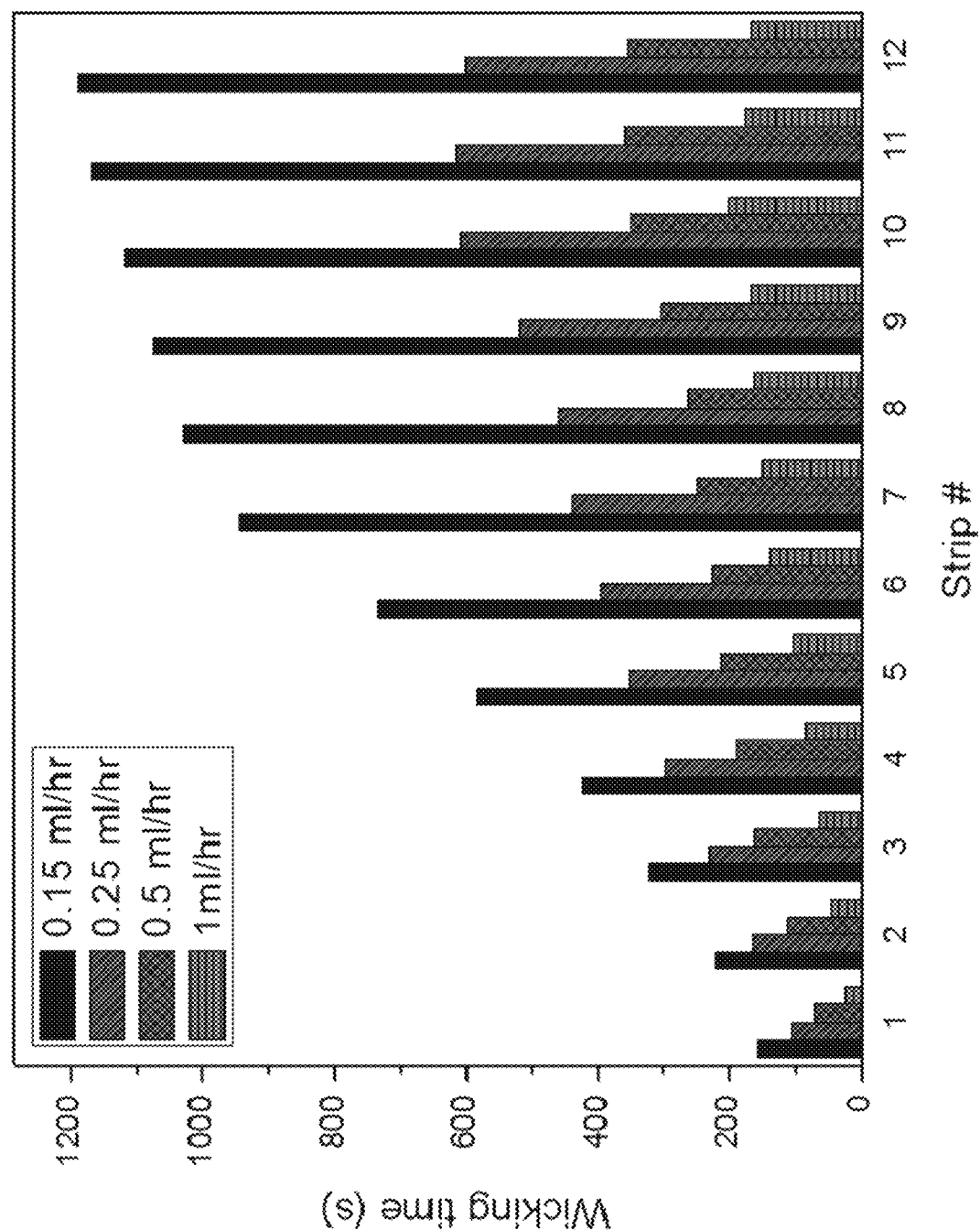
FIG. 6 is a graph illustrating the time required for each channel on a the device of FIG. 1 to be filled completely, as a function of the rate of introduction of water (representing sweating rate).

FIG. 4 illustrates a discrete wicking pattern as water (sweat) is deposited on the center hole at rates comparable to physiological sweat secretion rates during high-sweat conditions (~0.5 mL/hr for a 10 mm-diameter skin area on the back of the hand). The snapshots show that the spots become visible sequentially as the volume of water absorbed by the paper increases over time. The rate of wicking in the paper/Opsite bilayer was also characterized; the results (FIG. 5) reveal higher flowrates for wider strips, with values in the range 0.126-0.158 mm/s, sufficiently slow for a palm-sized patch to last for up to 20 minutes in heavy sweat conditions (or up to 3 h in moderate conditions). FIG. 6 shows the time required to fill each of the channels of the patch, ranging from 160 to 1190s when moisture is delivered at 0.15 mL/h. The patch is ideal for convenient and economical sweat monitoring.

Figure 7:
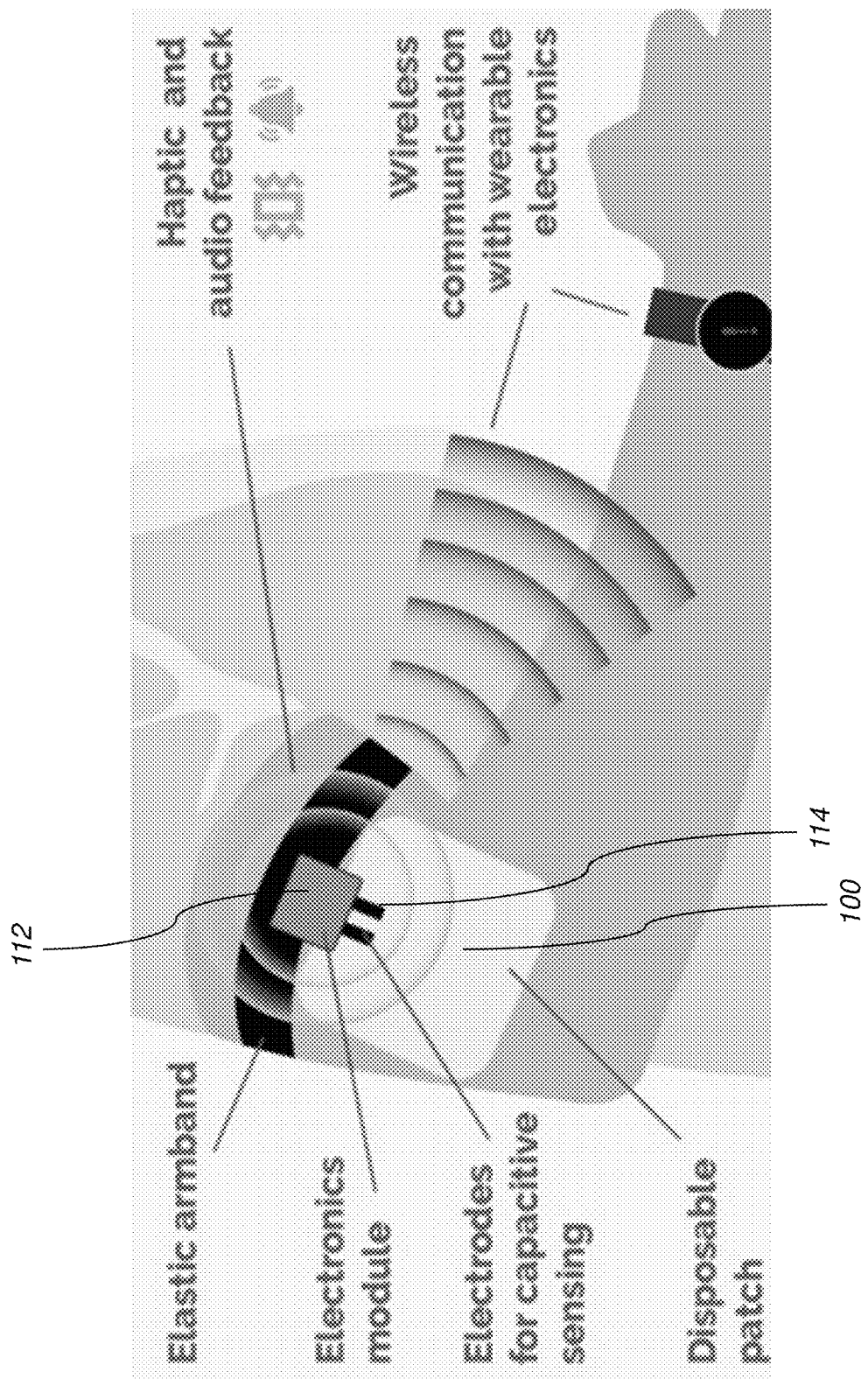
FIG. 7 is a diagram showing the patch of FIG. 1 installed on a user's arm, with an active capacitive sensing module attached to the patch and secured to the user's arm by an armband according to one embodiment.

FIG. 7 shows a further embodiment wherein the active module 112 is attached to an armband 120 while also attached to the device 100. As shown, the active module may wirelessly communicate with a device, such as a smartwatch 122, worn by the user to provide various forms of feedback regarding hydration as discussed above.

The microcontroller, sensors, and other components recited herein may include one or more computer processors and memory which are communicatively connected and programmed to perform the data processing and control functionality recited herein. The program code includes computer program instructions that can be loaded into the processor, and that, when loaded into processor cause functions, acts, or operational steps of various aspects herein to be performed by the processor. Computer program code for carrying out operations for various aspects described herein can be written in any combination of one or more programming language(s), and can be loaded into memory for execution. The processors and memory may further be communicatively connected to external devices via a wired or wireless computer network for sending and receiving data.

In the present disclosure the term "about" can allow for a degree of variability in a value or range, for example, within 10%, within 5%, or within 1% of a stated value or of a stated limit of a range.

The invention is inclusive of combinations of the aspects described herein. References to "a particular aspect" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:
1. A hydration sensor, comprising:
a hygroscopic substrate including a common central region and a plurality of fingers radially extending from the common central region and terminating at different corresponding lengths;
a first hydrophobic film layer covering an entirety of a first side of the hygroscopic substrate to protect the hygroscopic substrate from outside environment; and
a second hydrophobic film layer on a second side of the hygroscopic substrate, the second hydrophobic substrate comprising an adhesive surface;
wherein the second hydrophobic substrate defines an opening centrally positioned about the common central region to expose the common central region to the skin, wherein the hygroscopic substrate is configured to wick sweat hydration from the skin to each of the fingers.

2. The hydration sensor of claim 1, wherein the different corresponding lengths of the plurality of fingers are sized consecutively longer about the common central region.

3. The hydration sensor of claim 1, wherein each of the fingers comprise a hydration activated color sensor located near a distal end of the fingers.

4. The hydration sensor of claim 3, the hydration activated color sensor comprises a dye.

5. The hydration sensor of claim 4, the dye is $KMnO_4$ or $CuCl_2$.

6. The hydration sensor of claim 1, wherein the first hydrophobic film layer has a surface area that is between about 1 to about 100% larger than the hygroscopic substrate.

7. The hydration sensor of claim 1, the hygroscopic substrate is a hygroscopic film.

8. The hydration sensor of claim 7, the hygroscopic substrate is paper.

9. The hydration sensor of claim 1, further comprising a control circuitry having a computer processor and at least two electrodes which make contact with at least one of the fingers, the electrodes configured to measure a capacitance change resulting from the change in an amount of fluid in at least one of the fingers.

10. The hydration sensor of claim 1, further comprising feedback circuitry configured to provide feedback to the subject representing an amount of sweat being emitted by the skin.

11. The hydration sensor of claim 10, wherein the feedback comprises haptic feedback.

12. The hydration sensor of claim 10, wherein the feedback comprises audio.

13. The hydration sensor of claim 10, wherein the feedback comprises a visual output.

14. The hydration sensor of claim 13, wherein the feedback circuitry further comprises a light emitting diode.

* * * * *